(12) United States Patent
Yasui et al.

(10) Patent No.: US 7,118,601 B2
(45) Date of Patent: Oct. 10, 2006

(54) PARALLEL LINKAGE AND ARTIFICIAL JOINT DEVICE USING THE SAME

(75) Inventors: Yuji Yasui, Saitama-ken (JP); Hiroshi Kiyomoto, Saitama-ken (JP); Isao Usukura, Saitama-ken (JP); Youichi Nakahara, Saitama-ken (JP); Haruyuki Iwasaki, Saitama-ken (JP); Shungo Umeda, Saitama-ken (JP); Kazunori Yamamoto, Saitama-ken (JP); Masamitsu Shiono, Saitama-ken (JP); Kazuo Okada, Saitama-ken (JP); Manabu Nakayama, Saitama-ken (JP); Atsushi Kubo, Saitama-ken (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 169 days.

(21) Appl. No.: 10/376,169

(22) Filed: Feb. 28, 2003

(65) Prior Publication Data

US 2003/0163206 A1    Aug. 28, 2003

(30) Foreign Application Priority Data

Feb. 28, 2002    (JP)    ............................. 2002-054001

(51) Int. Cl.
*A61F 2/48*    (2006.01)
(52) U.S. Cl. ............................. 623/24; 403/53; 403/56; 403/377

(58) Field of Classification Search .................. 403/52, 403/53, 56, 57, 66, 122, 217, 377, 167, 186; 33/556; 74/479.01; 623/24, 27, 28, 32, 623/38, 47, 48, 52
See application file for complete search history.

(56) References Cited

U.S. PATENT DOCUMENTS 5,887,356 A * 3/1999 Sheldon ........................ 33/556
2003/0005786 A1 * 1/2003 Stuart et al. ............. 74/479.01

* cited by examiner

*Primary Examiner*—Corrine McDermott
*Assistant Examiner*—William H Matthews
(74) *Attorney, Agent, or Firm*—Lahive & Cockfield, LLP; Anthony A. Laurentano, Esq.

(57) ABSTRACT

There are provided an artificial joint device that can realize an artificial limb enabling twisting motion without a drive source, and when with the drive source, reduce the size and costs of the device, and a parallel linkage that can realize the device. The linkage connects a foot portion and a mounting plate spaced from each other. A fixed link has one end fixed to the plate, and the other end connected to the foot portion via a ball joint, making the angle of the fixed link relative to the foot portion changeable in any direction. Expansible links extend between the foot portion and the plate in an expansible/contractible manner and each have opposite ends connected to the plate and the foot portion via respective upper and lower ball joints, making respective angles thereof relative to the foot portion and the plate changeable in any direction.

3 Claims, 14 Drawing Sheets

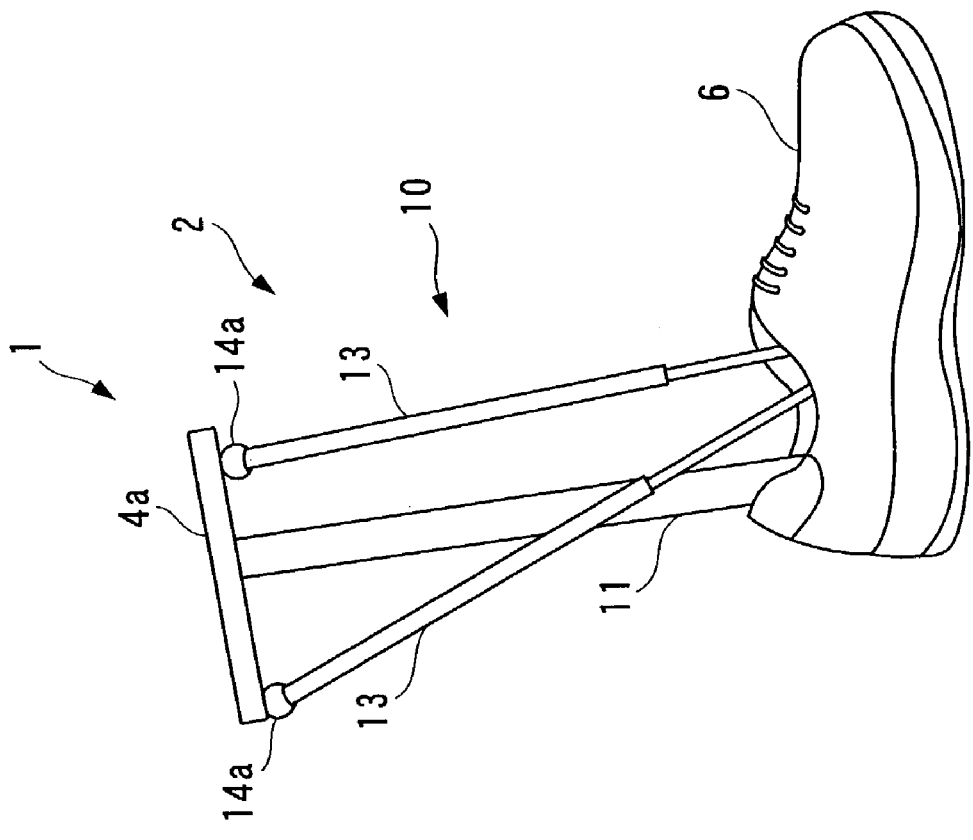
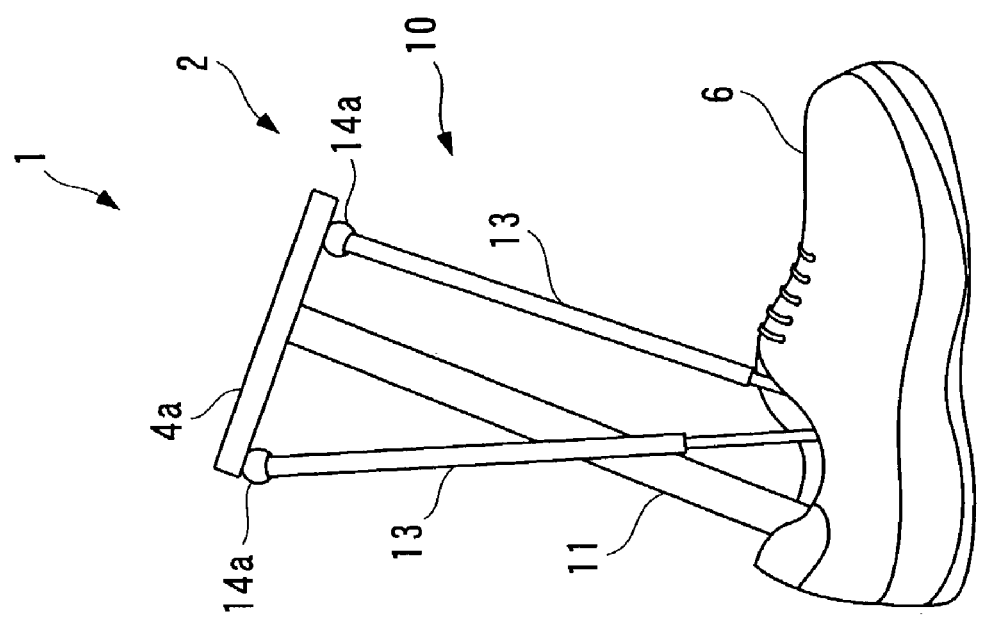

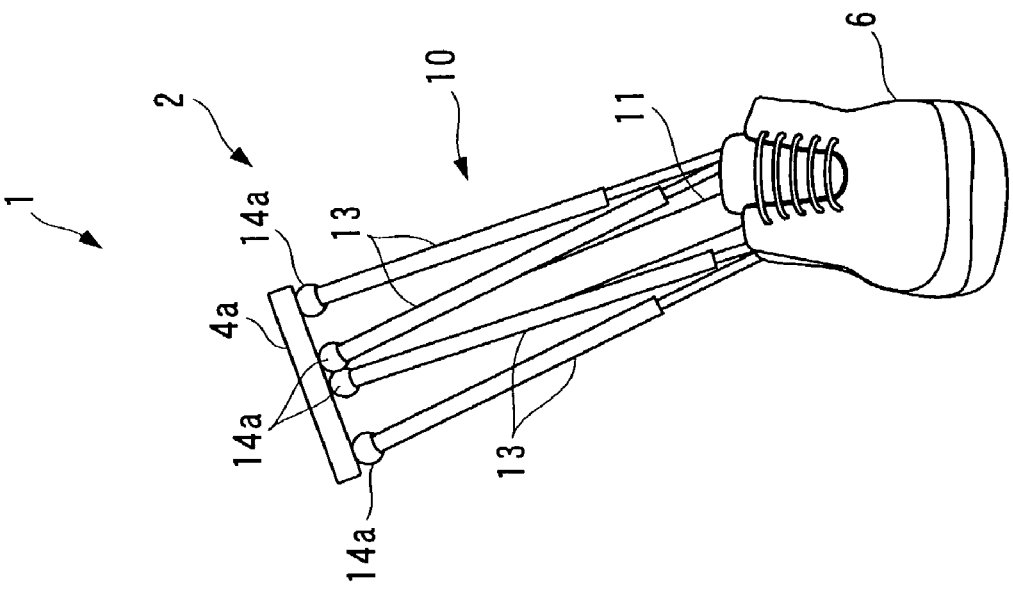
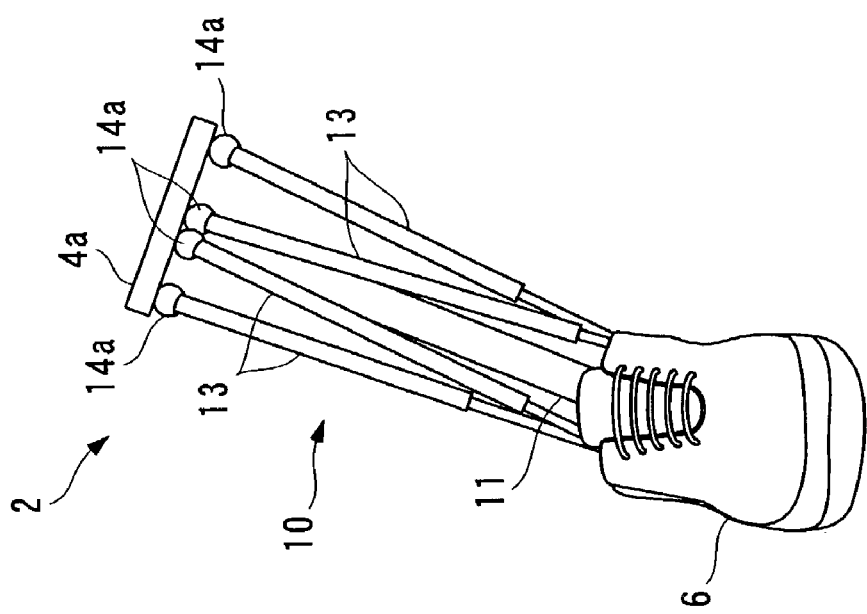

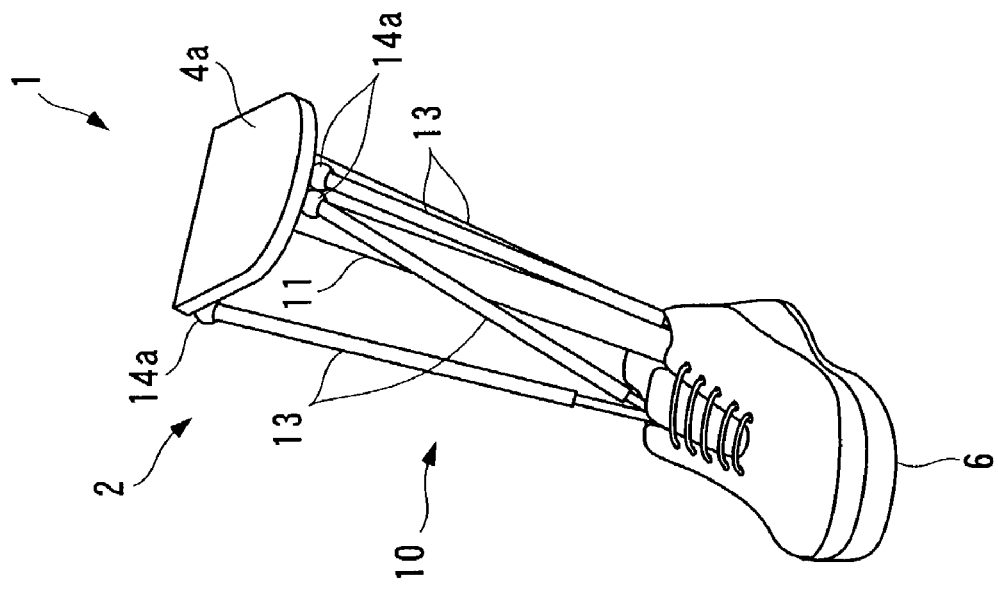
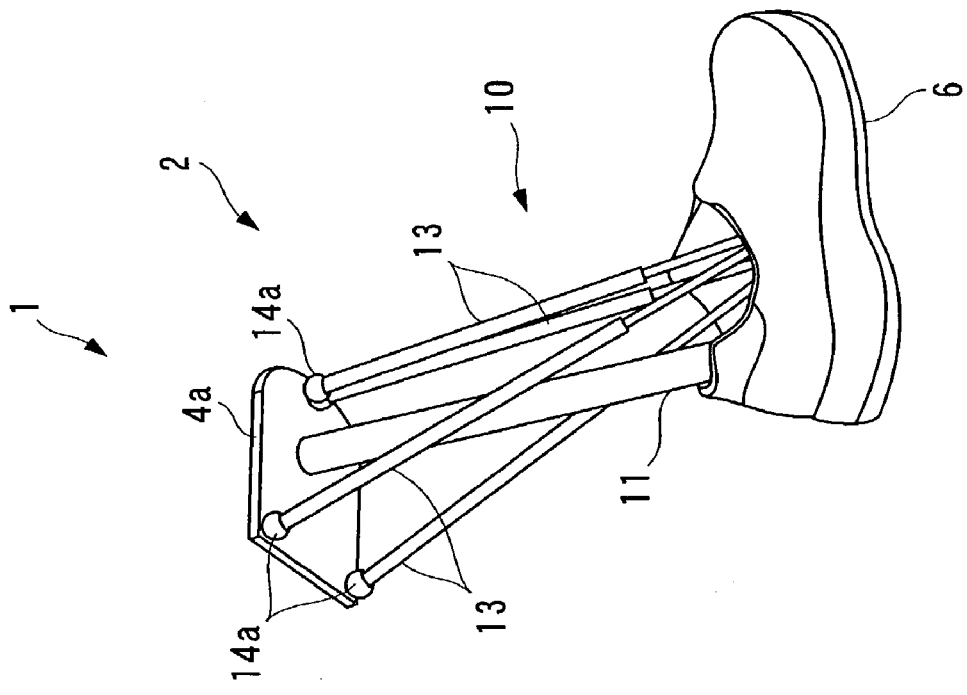

PARALLEL LINKAGE AND ARTIFICIAL JOINT DEVICE USING THE SAME

BACKGROUND OF THE INVENTION

1. Field of the Invention

This invention relates to an artificial joint device and a parallel linkage, which are applied to an artificial limb, such as a prosthetic limb or a limb of a robot.

2. Description of the Prior Art

Conventionally, an artificial joint device of the above-mentioned kind has been disclosed e.g. in Japanese Laid-Open Patent Publication (Kokai) No. 11-345. The artificial joint device is applied to an ankle joint for connecting between a foot portion of an artificial leg and a leg portion of the same. The foot portion of the artificial leg has an upper end portion thereof formed with a through hole extending laterally. On the other hand, the leg portion of the artificial leg has a lower end thereof bifurcated into two arms to form a bracket with each arm having a hole formed therethrough at a location corresponding to an opening of the through hole extending laterally through the foot portion. In this artificial joint device, a shaft is fitted through the holes of the bracket and the through hole of the foot portion, which are aligned with each other, whereby the foot portion and the leg portion are capable of performing pivotal motion with respect to each other about a horizontal axis, only in the front-rear direction.

According to the above conventional artificial joint device, since the foot portion and the leg portion are allowed to perform pivotal motion with respect to each other about the horizontal axis, only in the front-rear direction, even when a person wearing the artificial leg tries to turn left or right while walking, the ankle joint portion cannot be twisted, which makes the turning motion difficult to perform. A combination of a serial linkage having three or more degrees of freedom and electric motors, used as a joint portion of a limb of a robot, is known as an artificial joint device capable of performing the twisting motion. However, this kind of artificial joint device needs at least three electric motors so as to ensure the three or more degrees of freedom and at the same time support the weight of the components of the robot. This increases the size of a power supply and that of the whole device, resulting in increased manufacturing costs of the device. Further, the increased device size and the necessity of the power supply make it difficult to apply the device to a prosthetic limb.

SUMMARY OF THE INVENTION

It is an object of the invention to provide an artificial joint device which makes it possible to realize a prosthetic limb or the like capable of performing twisting motion without a drive source, and if the drive source is provided, achieve reduction of both the size and manufacturing costs of the artificial joint device itself, and a parallel linkage which makes it possible to realize the artificial joint device.

To attain the above object, according to a first aspect of the invention, there is provided a parallel linkage for connecting two link mounting portions spaced from each other, comprising:

a fixed link having one end thereof fixed to one of the link mounting portions;

a fixed-link joint for connecting another end of the fixed link to another of the link mounting portions such that an angle of the fixed link with respect to the another of the link mounting portions can be changed in any desired direction;

a plurality of expansible links extending between the two link mounting portions in an expansible/contractible manner; and a plurality of expansible-link joints respectively connecting opposite ends of the plurality of expansible links to the link mounting portions such that respective angles of each expansible link with respect to the link mounting portions can be changed in any desired direction.

According to this parallel linkage, one end of the fixed link is fixed to one of the link mounting portions. Therefore, by making the fixed link solid and robust, it is possible to bear most of compressive load or tensile load applied to at least one of the link mounting portions by the fixed link. In addition, since each of the plurality of expansible links has the opposite ends thereof connected to the two link mounting portions via expansible-link joints associated therewith, respectively, such that the angles thereof with respect to the respective link mounting portions can be changed in any desired direction, no bending stress is applied to the expansible links, but only compressive load and/or tensile load are applied to the same. This makes it possible to use expansible links having relatively low strength and rigidity, thereby reducing the weight of the parallel linkage. Further, the other end of the fixed link and the opposite ends of the expansible links are each connected to the corresponding link mounting portion via the fixed-link joint or the expansible-link joint such that the angle thereof with respect to the link mounting portion can be changed in any desired direction, which ensures a high degree of freedom in the angle of relative motion between the two link mounting portions to thereby enable e.g. twisting motion therebetween.

Preferably, the parallel linkage further comprises urging members provided in the plurality of expansible links, respectively, each for urging a corresponding one of the expansible links in at least one opposite direction to directions in which the expansible link expands and contracts, when the expansible link expands and contracts.

According to this preferred embodiment, since each expansible link is urged by the corresponding urging member in a direction or directions opposite to the expanding direction and/or the contracting direction, it is possible to reduce shock transmitted between the two link mounting portions via the expansible links, by the urging forces. Further, as the amount of contraction or expansion of the expansible link is larger, the urging force of the corresponding urging member is increased, so that the movable range of the expansible link can be properly limited so as to prevent the link mounting portions from moving more than necessary. As a result, even when the link mounting portions are moved e.g. along a curved surface or a three-dimensional object, it is possible to prevent occurrence of wobbling, thereby maintaining excellent follow-up performance.

Preferably, the fixed link includes a shock-absorbing member for absorbing shock transmitted between the two link mounting portions.

According to this preferred embodiment, it is possible to absorb shock transmitted between the two link mounting portions via the fixed link, by the shock-absorbing member.

Preferably, the plurality of expansible links are at least three expansible links.

According to this preferred embodiment, since the two link mounting portions are connected to each other via at least three expansible links and the fixed link, when the expansible links are each actuated e.g. by an actuator for expansion and contraction, it is possible to actuate the expansible links in a manner such that the expansible links twist the two link mounting portions in respective opposite rotating directions.

More preferably, the at least three expansible links are arranged such that connecting portions thereof connected to at least one of the two link mounting portions are not in a line on the at least one of the two link mounting portions, and that a connecting portion of the fixed link is positioned within a polygon defined by the connecting portions of the at least three expansible links as vertexes.

According to this preferred embodiment, since the at least three expansible links are arranged such that connecting portions thereof connected to at least one of the two link mounting portions are not in a line on the link mounting portion, and that a connecting portion of the fixed link is positioned within a polygon defined by the connecting portions of the at least three expansible links as vertexes, it is possible to make compact in size the parallel linkage capable of twisting the two link mounting portions in the respective opposite rotating directions as described above. Further, a driving force required for causing the twisting operation can be reduced, which contributes to enhancement of operating efficiency.

More preferably, the parallel linkage further comprises a drive source, actuators each for actuating a corresponding one of the at least three expansible links for expansion and contraction by a driving force supplied from the drive source, and control means for controlling the driving force supplied to the each actuator from the drive source.

According to this preferred embodiment, since the control means can control expansion and contraction of each of the at least three expansible links via the actuator, it is possible to actuate the expansible links to twist the two link mounting portions in the respective opposite rotating directions as described above, and hence the parallel linkage can be applied to a robot and an industrial machine necessitating such twisting motions. Further, as described hereinbefore, when the fixed link is made solid and robust, the fixed link can bear most of compressive load and tensile load applied to at least one of the link mounting portions, which enables reduction of the driving forces supplied to the actuators for actuating the expansible links, thereby contributing to reduction of energy consumption.

Further preferably, the actuator is an electric actuator configured to produce regenerative power when the corresponding expansible link is expanded and contracted by an external force, and the parallel linkage further comprises an accumulator for storing the regenerative power produced by the electric actuator.

According to this preferred embodiment, since the electric actuators are capable of producing regenerative power when the expansible links are expanded and contracted by external forces, it is possible to utilize the regenerative power as electric power for driving the electric actuators. This makes it possible to reduce both the size of a power supply and the running costs, which contributes to reduction of manufacturing costs of the parallel linkage.

To attain the above object, according to a second aspect of the invention, there is provided an artificial joint device comprising:

two limb members spaced from each other; and
a parallel linkage connecting the two limb members.

According to this artificial joint device, since the two limb members are connected by the parallel linkage, it is possible to enhance the degree of freedom in the angle of relative motion between the two limb members to a level similar to that of a joint of a living body, which has been unattainable by the artificial joint device of the conventional artificial leg. Further, differently from an artificial joint device of a serial linkage type conventionally used e.g. in a robot, the artificial joint device according to this aspect of the invention can be realized without using any power supply or electric motor, but by using the parallel linkage which is simpler and less expensive than the serial linkage.

Preferably, the parallel linkage comprises a fixed link having one end thereof fixed to one of the limb members, a fixed-link joint for connecting another end of the fixed link to another of the limb members such that an angle of the fixed link with respect to the another of the limb members can be changed in any desired direction, a plurality of expansible links extending between the two limb members in an expansible/contractible manner, and a plurality of expansible-link joints respectively connecting opposite ends of the plurality of expansible links to the limb members such that respective angles of each expansible link with respect to the limb members can be changed in any desired direction.

According to this preferred embodiment, the same advantageous effects as provided by the above parallel linkage can be obtained. More specifically, it is possible to reduce the weight of the artificial joint device and achieve a high degree of freedom of the same. Therefore, when the artificial joint device is applied e.g. to an ankle joint of an artificial leg, it is possible to reduce the weight of the artificial leg, and at the same time, differently from the artificial joint of the conventional artificial leg, the artificial joint of the preferred embodiment enables a user to perform e.g. twisting motion or the like between a leg portion and a foot portion, similarly to an ankle joint of a living leg, while support his weight by the artificial leg. This enables the user to perform smoother and more natural motion not only in walking straight ahead but also in turning left or right while walking. Similarly, when the artificial joint device is applied e.g. to a wrist joint of an artificial arm, the weight of the artificial arm can be reduced, and at the same time, the artificial joint enables twisting motion or the like to be performed between an arm portion and a hand portion. In short, the artificial joint makes it possible to enhance the degree of freedom in the angle of motion between the arm portion and the hand portion.

More preferably, the artificial joint device further comprises urging members provided in the plurality of expansible links, respectively, each for urging a corresponding one of the expansible links in at least one opposite direction to directions in which the expansible link expands and contracts, when the expansible link expands and contracts.

According to this preferred embodiment, the same advantageous effects as provided by the above parallel linkage can be obtained. More specifically, it is possible to absorb shock transmitted between the two limb members via the expansible links. Therefore, when the artificial joint device is applied e.g. to an ankle joint of an artificial leg, the urging members serve to soften shock transmitted from the artificial leg to a user's living body via the expansible links when the user puts the artificial leg on a floor, a road surface, or the like (hereinafter simply referred to as "the floor"), to thereby reduce burden on the user wearing the artificial leg. In addition, if the urging members urge the respective expansible links when they contract, in a direction opposite to the contracting direction, when the user is lifting the artificial leg up from the floor while walking, urging forces urging the artificial leg to kick against the floor can be obtained, and hence it is possible to reduce a kicking force from the walking living body, thereby further reducing burden on the user wearing the artificial leg, and enabling the user to perform smoother walking motion. Further, even when the walking motion demands the angle of the ankle to follow up a road surface and a proper holding force of the ankle joint, e.g. in the case of walking up or down a slope, the demanded follow-up performance and holding force can be ensured by the urging forces of the urging members.

More preferably, the fixed link includes a shock-absorbing member for absorbing shock transmitted between the two limb members.

According to this preferred embodiment, the same advantageous effects as provided by the above parallel linkage can be obtained. More specifically, it is possible to absorb shock transmitted between the two limb members via the fixed link. Therefore, when the artificial joint device is applied e.g. to an artificial leg, it is possible to soften shock transmitted from the artificial leg to a user's living body via the fixed link when the user puts the artificial leg on the floor, to thereby further reduce the burden on the user of the artificial leg.

More preferably, the plurality of expansible links are at least three expansible links.

According to this preferred embodiment, the same advantageous effects as provided by the above parallel linkage can be obtained. More specifically, when the expansible links are each driven e.g. by an actuator for expansion and contraction, it is possible to operate the expansible links to twist the two limb members in respective opposite rotating directions, and realize an automatically controlled artificial joint device having such a twisting capability.

Further preferably, the at least three expansible links are arranged such that connecting portions thereof connected to at least one of the two limb members are not in a line on the at least one of the two limb members, and that a connecting portion of the fixed link is positioned within a polygon defined by the connecting portions of the at least three expansible links as vertexes.

According to this preferred embodiment, the same advantageous effects as provided by the above parallel linkage can be obtained. More specifically, it is possible to make compact in size the automatically controlled artificial joint device capable of twisting the two limb members in the respective opposite rotating directions. Further, a driving force required for causing the twisting motion can be reduced, which contributes to enhancement of operating efficiency.

Further preferably, the artificial joint device further comprises a drive source, actuators each for actuating a corresponding one of the at least three expansible links for expansion and contraction by a driving force supplied from the drive source, and control means for controlling the driving force supplied to the each actuator from the drive source.

According to this preferred embodiment, the same advantageous effects as provided by the above parallel linkage can be obtained. More specifically, it is possible to twist the two limb members in the respective opposite rotating directions. Therefore, when the artificial joint device is applied e.g. to an ankle joint of an artificial leg, it is possible to enable the user to perform twisting of an ankle thereof and smooth turning motion in walking, as well as to realize an automatically controlled artificial leg having such a twisting capability. Further, when the artificial joint device is applied to a joint at the ball of the foot of the artificial leg, the artificial leg enables still smoother turning motion in walking, so that it is possible to approximate the motion of the automatically controlled artificial leg to that of a living leg. Besides, by making the fixed link solid and robust, as described hereinbefore, it is possible to cause the fixed link to bear load from the weight of a user, which enables reduction of the driving forces supplied to the actuators, thereby contributing to reduction of energy consumption by the automatically controlled artificial leg. Similarly, when the artificial joint device is applied to a wrist joint or a joint at a thenar of an artificial arm, it is possible to realize an automatically controlled artificial hand or arm. The use of the artificial joint device makes it possible not only to approximate the motion of the artificial hand or arm to that of a living hand or arm, but also to reduce energy consumption. Further, when the artificial joint device is applied to a limb of a robot, it is also possible to obtain the same effects as described above.

Even more preferably, the actuator is an electric actuator configured to produce regenerative power when the corresponding expansible link is expanded and contracted by an external force, and the artificial joint device further comprises an accumulator for storing the regenerative power produced by the electric actuator.

According to this preferred embodiment, the same advantageous effects as provided by the above parallel linkage can be obtained. Therefore, when the artificial joint device is applied to a prosthetic limb or a limb of a robot, it is possible to reduce both the size of the power supply and running costs, which contributes to reduction of costs of the prosthetic limb or the robot.

Even more preferably, the artificial joint device is used in at least one of an artificial leg and an artificial arm, and further comprises operating will-detecting means for detecting a user's operating will to operate the at least one of the artificial leg and the artificial arm, and the control means controls the actuators according to the sensed operating will.

According to this preferred embodiment, operating will of a user using the artificial leg and/or the artificial arm is detected by the operating will-detecting means, and the actuators are controlled by the control means according to the sensed operating will. In general, the motion of a joint of a living body, particularly the motion of a joint of a limb is complicated, so that when a parallel linkage using actuators is used to imitatively realize the complicated motion, it is impossible to control the parallel linkage directly by an instruction or the like from a user's brain. For this reason, a control system is needed to detect the user's operating will from operations of the user's brain, nerves, and/or muscles and control the parallel linkage according to the sensed operating will. Therefore, the artificial joint device makes it possible to cause the motion of the automatically controlled artificial leg and/or artificial arm to match or conform with a motion intended by the user, thereby enhancing convenience of the artificial leg and/or artificial arm.

Preferably, the parallel linkage comprises an inexpansible movable link extending between the two limb members, and two movable-link joints for connecting opposite ends of the inexpansible movable link to the two limb members, respectively, such that respective angles of the inexpansible movable link with respect to the limb members can be changed in any desired direction.

According to this preferred embodiment, since the opposite ends of the inexpansible movable link are connected to the two limb members, respectively, such that respective angles of the inexpansible movable link with respect to the limb members can be changed in any desired direction, it is possible to maintain a constant distance between the portions of the respective limb members connected to the inexpansible movable link as well as to constrain a superfluous degree of freedom of the parallel linkage and limit unnecessary motion of the same.

Preferably, the artificial joint device is used for a hallux portion, and the parallel linkage includes at least three expansible links extending between the two limb members in an expansible/contractible manner, and a plurality of expansible-link joints respectively connecting opposite ends of the at least three expansible links to the limb members such that respective angles of each expansible link with respect to the limb members can be changed in any desired direction, the artificial joint device further comprising a drive source, actuators each for actuating a corresponding one of the at least three expansible links for expansion and contraction by a driving force supplied from the drive source, and control means for controlling the driving force supplied to the each actuator from the drive source.

Preferably, the artificial joint device is used for a thumb portion, and the parallel linkage includes at least three expansible links extending between the two limb members in an expansible/contractible manner, and a plurality of expansible-link joints respectively connecting opposite ends of the at least three expansible links to the limb members such that respective angles of each expansible link with respect to the limb members can be changed in any desired direction, the artificial joint device further comprising a drive source, actuators each for actuating a corresponding one of the at least three expansible links for expansion and contraction by a driving force supplied from the drive source, and control means for controlling the driving force supplied to the each actuator from the drive source.

According to these preferred embodiments, since the opposite ends of each of the at least three expansible links are respectively connected to the limb members such that respective angles of the expansible link with respect to the limb members can be changed in any desired direction, it is possible to achieve a high degree of freedom of a joint at the ball of the foot (joint to a hallux (big toe)) or a joint at a thenar (joint to a thumb). In addition, since the operations of the actuators actuating the respective expansible links are controlled by the control means, it is possible to realize an automatically controlled joint at the ball of the foot or at the thenar. Therefore, when the artificial joint device is applied to a joint at the ball of the foot (joint to a hallux) of an artificial foot or leg, the motion of the hallux which plays an important role in turning motion of the artificial foot or leg performed during walking, can be approximated to that of a living hallux. Thus, it is possible to approximate the walking motion, including turning motion, of the automatically controlled artificial foot or leg to that of a living foot or leg, thereby enabling smooth walking motion of the artificial foot or leg. Similarly, when the artificial joint device is applied to a joint at a thenar (joint to a thumb) of an artificial hand or arm, it is possible to approximate the degree of freedom in the motion of the automatically controlled artificial hand or arm to that of a living hand or arm. Further, when the artificial joint device is applied to a joint of a limb of a robot, it is possible to obtain the same advantageous effects as described above.

More preferably, the parallel linkage comprises an inexpansible movable link extending between the two limb members, and two movable-link joints for connecting opposite ends of the inexpansible movable link to the two limb members, respectively, such that respective angles of the inexpansible movable link with respect to the limb members can be changed in any desired direction.

According to this preferred embodiment, the same advantageous effects as described above can be obtained. In addition, since it is possible to bend the joint to the hallux or thumb without changing the length of the hallux or thumb, the motion of the hallux or thenar of the automatically controlled prosthetic limb can be further approximated to that of the living hallux or thumb.

More preferably, the control means controls the driving force supplied to the each actuator from the drive source such that a distance between the two limb members is held constant.

According to this preferred embodiment, it is possible to further approximate the motion of the joint to the hallux or thumb of the automatically controlled prosthetic limb to that of the living hallux or thumb without increasing component parts of the prosthetic limb in number.

The above and other objects, features, and advantages of the invention will become more apparent from the following detailed description taken in conjunction with the accompanying drawings.

BRIEF DESCRIPTION OF THE DRAWINGS

FIG. 5A is a side view of the right artificial leg in a state in which an ankle joint thereof is bent forward during walking;

FIG. 5B is a side view of the right artificial leg in a state in which the ankle joint is bent backward;

FIG. 6A is a front view of the right artificial leg in a state in which the ankle joint is bent leftward during walking;

FIG. 6B is a front view of the right artificial leg in a state in which the ankle joint is bent rightward;

FIGS. 7A and 7B are perspective views of the right artificial leg in a state in which the ankle joint is twisted leftward when leftward turning motion is performed during walking;

DETAILED DESCRIPTION OF PREFERRED EMBODIMENTS

The invention will now be described in detail with reference to drawings showing preferred embodiments thereof.

Figure 1:
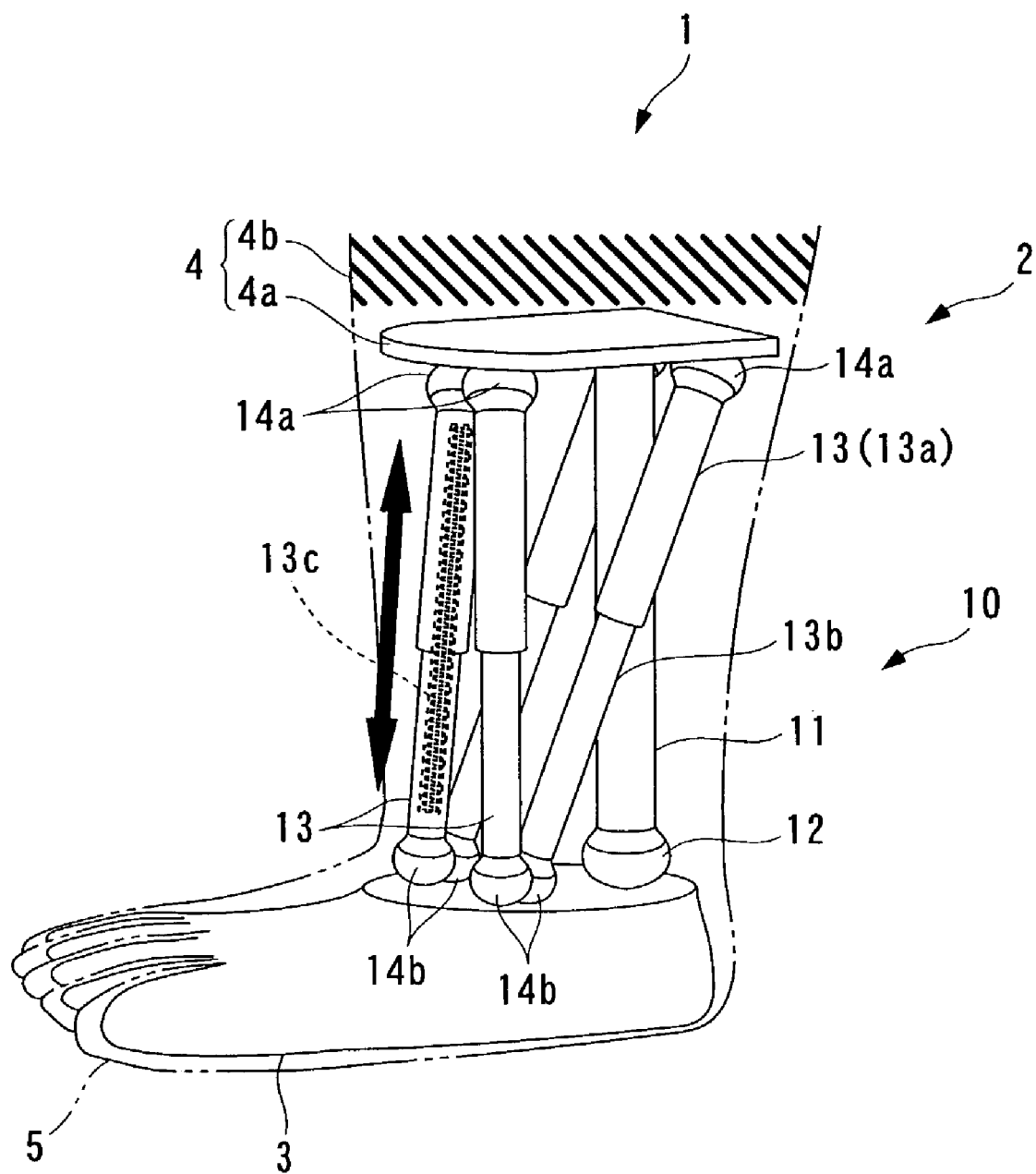
FIG. 1 is a view schematically showing the construction of a right artificial leg incorporating an artificial joint device including a parallel linkage according to a first embodiment of the invention.

Referring first to FIG. 1, there is schematically shown the construction of an artificial leg 1 in which an artificial joint device 2 including a parallel linkage according to a first embodiment of the invention is applied to an ankle joint thereof. In the following description, the left and right sides and the front and rear sides as viewed from a user wearing the artificial leg are referred to as the left and right sides and the front and rear sides, respectively (more specifically, the left and right sides as viewed in FIG. 1 are referred to as the front and rear sides, respectively, and the front and rear sides as viewed in the same are referred to as the left and right sides, respectively).

As shown in the figure, the artificial leg 1 is a type attached to an under-knee leg portion of a living body, and used for a right leg. The artificial leg 1 includes a foot portion 3 and a leg mounting portion 4, the artificial joint device 2 connecting these portions by a parallel linkage 10, and a cover 5. The whole of the artificial leg 1, including the artificial joint device 2, is covered with the cover 5, such that it has an appearance generally similar to that of a living leg.

The foot portion 3 (link mounting portion, limb member) is similar in shape to a living foot, and has a flat upper end face. The leg mounting portion 4 is comprised of a flat mounting plate 4a and a prosthetic liner 4b. In attaching the artificial leg 1 to a living under-knee leg portion, not shown, of the user, the mounting plate 4a (link mounting portion, limb member) is connected to the living under-knee leg portion via a fastener, not shown, with the prosthetic liner 4b interposed between the under-knee leg portion and the mounting plate 4a itself. The prosthetic liner 4b is formed e.g. of porous silicon. When the mounting plate 4a is connected to the living under-knee leg portion, the prosthetic liner 4b deforms to conform to the under-knee leg portion and combine the under-knee leg portion and the mounting plate 4a in a state in which they are kept from direct contact with each other. This makes it possible to reduce unnatural and unpleasant feeling of the user, thereby enhancing his feeling of wearing the artificial leg.

The parallel linkage 10 includes one fixed link 11 and four expansible links 13. The fixed link 11 has an upper end thereof fixed to the mounting plate 4a and a lower end thereof connected to the foot portion 3 via a ball joint 12 (fixed-link joint). This construction enables the fixed link 11 to pivotally move in any desired direction with respect to the foot portion 3. In short, the fixed link 11 has at least three degrees of freedom.

Each of the four expansible links 13 has an upper end thereof connected to the mounting plate 4a via an upper ball joint 14a (expansible-link joint) and a lower end thereof connected to the foot portion 3 via a lower ball joint 14b (expansible-link joint). Each adjacent two of the four expansible links 13 is arranged such that a space (or distance) between them is progressively reduced either in an upward direction or in a downward direction. More specifically, the right and left expansible links 13, 13 on the front side are arranged with a space therebetween progressively decreased in the upward direction, and the upper ball joints 14a, 14a at the respective upper ends of the two expansible links 13, 13 are arranged on the lower surface of the mounting plate 4a at respective locations close to each other. On the other hand, each two expansible links 13, 13 in the front-rear direction are arranged with a space (distance) therebetween progressively decreased in the downward direction, and the lower ball joints 14b, 14b at the respective lower ends of the two expansible links 13, 13 are arranged on the flat upper end face of the foot portion 3 at respective locations close to each other.

Figure 2:
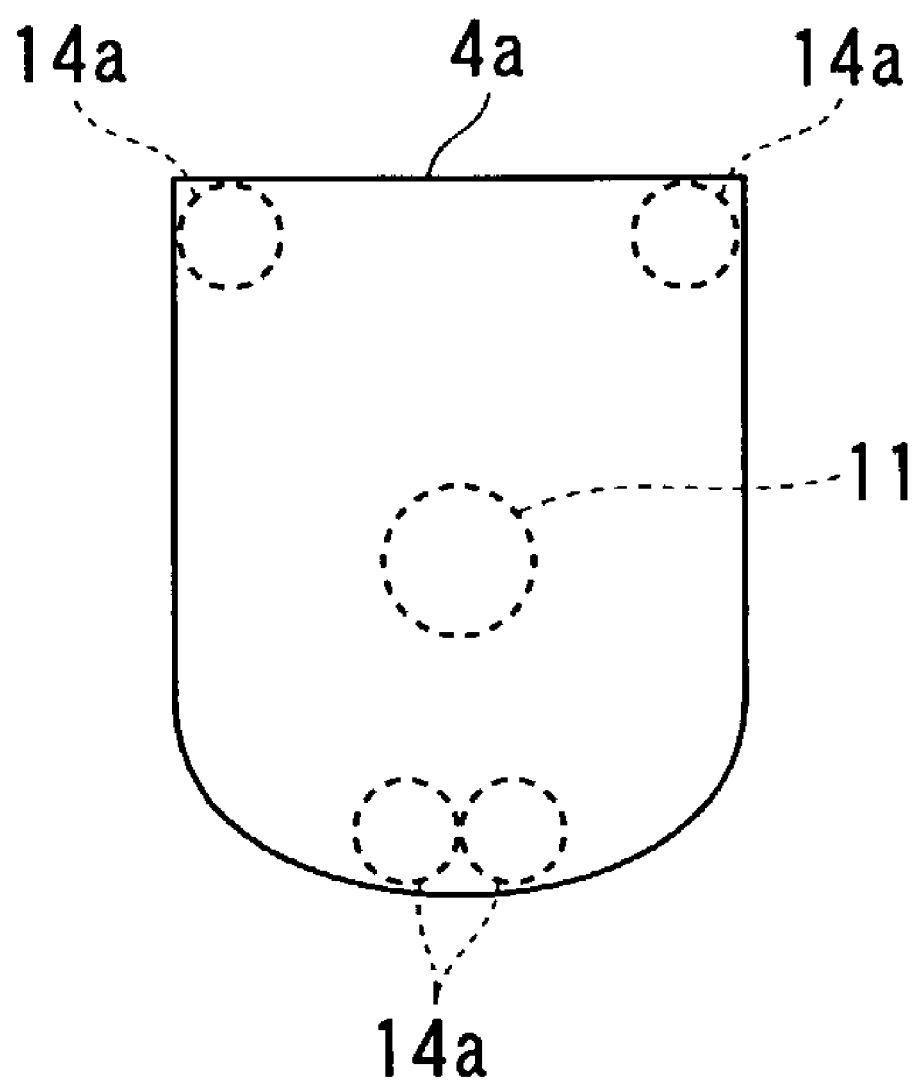
FIG. 2 is a plan view showing the positional relationship on a mounting plate between four upper ball joints and a connecting portion of a fixed link.

Further, as shown in FIG. 2, the four upper ball joints 14a connecting the respective upper ends of the four expansible links 13 to the mounting plate 4a are positioned on the lower surface of the mounting plate 4a such that they are not arranged in a line, and that a connecting portion of the fixed link 11 via which the fixed link 11 is connected to the mounting plate 4a is located within a quadrilateral defined by the upper ball joints 14a as vertexes.

Each of the expansible links 13 is comprised of upper and lower cylinders 13a, 13b slidably fitted to each other and a coil spring 13c received within the cylinders 13a, 13b. The lower cylinder 13b is smaller in diameter than the upper cylinder 13a and fitted in a bore of the upper cylinder 13a. This construction enables the two cylinders 13a, 13b to slide relative to each other in an axial direction, and thereby enables the expansible link 13 to axially expand and contract.

Further, the upper cylinder 13a has an upper end thereof closed by a lid, not shown, to which is attached the upper end of the coil spring 13c. Similarly, the lower cylinder 13b has a lower end thereof closed by a lid, not shown, to which is attached the lower end of the coil spring 13c. According to this construction, when the expansible link 13 expands to a larger length than a predetermined reference length, the coil spring 13c (urging member) is pulled and stretched by the motion of the expansible link 13, to urge the expansible link 13 in a contracting direction. On the other hand, when the expansible link 13 contracts to a smaller length than the predetermined reference length, the coil spring 13c is compressed by the motion of the expansible link 13, to urge the expansible link 13 in an expanding direction.

The operation of the artificial leg 1 constructed as above will be described with reference to FIGS. 3A to 7B. It should be noted that in the artificial leg 1 shown in the figures, a shoe 6 is fitted on the foot portion 3, and the cover 5 and the prosthetic liner 4b are omitted for clarity. Further, in the figures, the living under-knee leg portion to which the artificial leg 1 is attached is omitted from illustration.

Figure 3A:
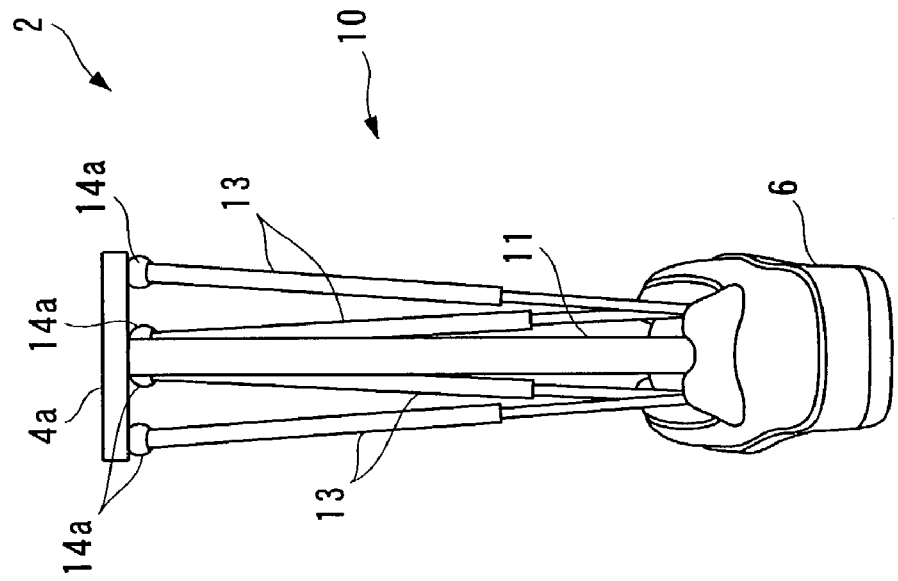
FIG. 3A is a front view of the right artificial leg in a detached state.
Figure 3B:
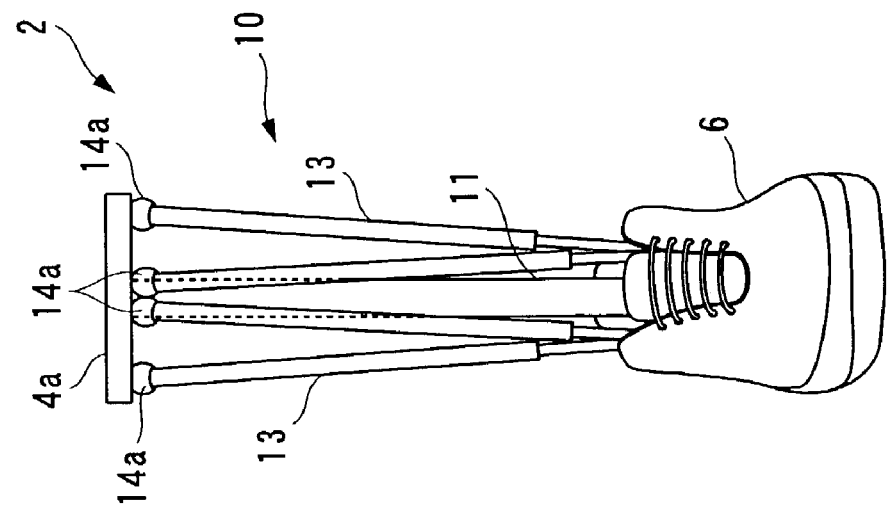
FIG. 3B is a rear view of the right artificial leg in the detached state.
Figure 4:
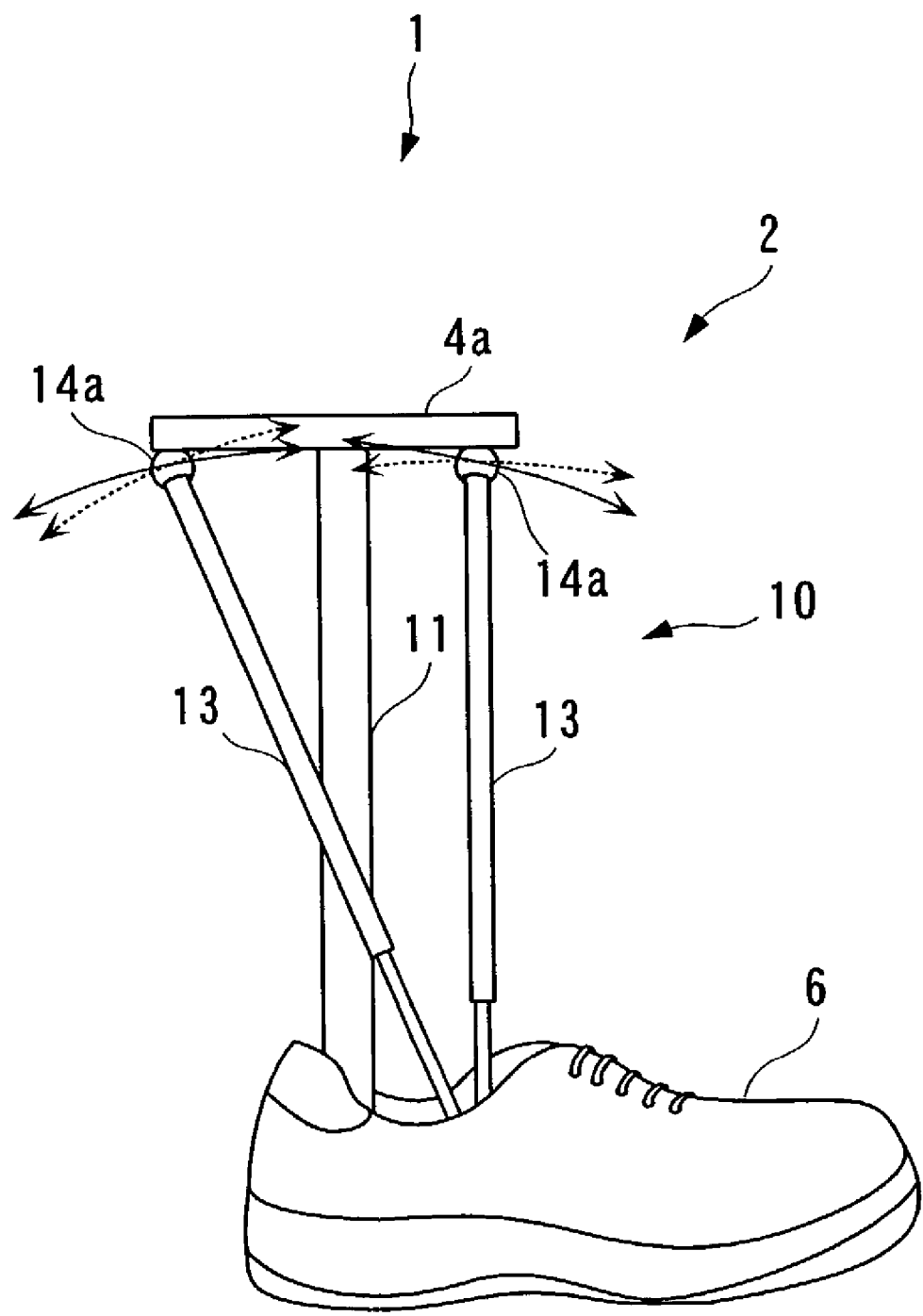
FIG. 4 is a side view of the right artificial leg in the detached state.

First, in a state detached from the living under-knee leg portion, the artificial leg 1 is held in a substantially erected state by the urging force of the coil spring 13c within each expansible link 13 as shown in FIGS. 3A, 3B and 4. As illustrated in FIG. 4, assuming that a front expansible link 13 performs pivotal motion freely about the corresponding lower ball joint 14b, the center of the upper ball joint 14a at the upper end of the expansible link 13 may be expected to move in a circular arc shown by a broken line, but actually, it moves in a circular arc shown by a solid line, more specifically along a circular arc drawn with the lower ball joint 12 of the fixed link 11 as its center. Accordingly, the front expansible link 13 is compressed when the artificial leg 1 tilts forward from a position shown in FIG. 4, and expanded when the artificial leg 1 tilts backward. In these operations, since the upper and lower ends of the expansible link 13 are connected to the mounting plate 4a and the foot portion 3, respectively, via the upper and lower ball joints 14a, 14b, no bending stress is applied to the front expansible links 13, but only compressive load and/or tensile load are applied to the same.

Similarly to the front expansible link 13, assuming that a rear expansible link 13 performs pivotal motion freely about the corresponding lower ball joint 14b, the center of the upper ball joint 14a at the upper end of the expansible link 13 may be expected to move in a circular arc shown by a broken line, but actually, it moves in a circular arc shown by a solid line, more specifically along a circular arc drawn with the lower ball joint 12 of the fixed link 11 as its center. Accordingly, the rear expansible link 13 is also compressed when the artificial leg 1 tilts forward from the position shown in FIG. 4, and expanded when the artificial leg 1 tilts backward. In these operations, for the same reason as described above, no bending stress is applied to the rear expansible links 13, but only compressive load and/or tensile load are applied to the same.

Therefore, when the user wearing the artificial leg 1 at the living under-knee leg portion tilts the under-knee leg portion forward while walking, as shown in FIG. 5A, the four expansible links 13 are all compressed as described above. At this time point, since the lower ball joints 14b of the four expansible links 13 are positioned at the respective locations forward of the ball joint 12 of the fixed link 11, the urging forces of the four coil springs 13c act to cause the foot portion 3 to pivotally move toward a floor about the ball joint 12 of the fixed link 11, while reaction forces from the floor act to push the living under-knee leg portion in an obliquely upward and forward direction. As a result, motion of kicking against the floor by the artificial leg 1 is promoted, which enables nimbler and smoother walking motion.

On the other hand, when the user tilts the under-knee leg portion backward while walking, as shown in FIG. 5B, the four expansible links 13 are all expanded as described above. At this time point, since the lower ball joints 14b of the four expansible links 13 are positioned as described above, the urging forces of the four coil springs 13c act to cause the fixed link 11 to pivotally move forward about the ball joint 12 thereof. As a result, motion of moving the knee forward is promoted, which enables nimbler and smoother walking motion.

Further, as shown in FIG. 6A, when the under-knee leg portion is tilted leftward, two expansible links 13 on the left side are both compressed, while two expansible links 13 on the right side are both expanded. This occurs because the center of the upper ball joint 14a of each expansible link 13 moves in a circular arc about the lower ball joint 12 at the lower end of the fixed link 11 as described above. At this time point, the urging forces of the four coil springs 13c act to cause the fixed link 11 to pivotally move rightward about the ball joint 12 thereof. In short, the urging forces act to return the fixed link 11 to the state shown in FIGS. 3A, 3B.

On the other hand, as shown in FIG. 6B, when the under-knee leg portion is tilted rightward, two expansible links 13 on the right side are both compressed, while two expansible links 13 on the left side are both expanded. At this time point, the urging forces of the four coil springs 13c act to cause the fixed link 11 to pivotally move leftward about the ball joint 12 thereof. In short, the urging forces act to return the fixed link 11 to the state shown in FIGS. 3A, 3B.

Further, when the under-knee leg portion is tilted leftward and twisted about the foot portion 3 as shown in FIGS. 7A, 7B so as to turn left, the urging forces of the four coil springs 13c act to return the same to the state shown in FIGS. 3A, 3B while twisting the fixed link 11 rightward.

According to the above parallel linkage 10, the upper end of the fixed link 11 is fixed to the mounting plate 4a. Therefore, by making the fixed link 11 solid and robust, it is possible to bear most of the user's weight acting on the mounting plate 4a or most of the reaction force that the foot portion 3 receives from the floor. In addition, since each of the four expansible links 13 has the upper and lower ends thereof connected to the mounting plate 4a and the foot portion 3 via the ball joints 14a, 14b, respectively, such that the angle thereof with respect to the mounting plate 4a or the foot portion 3 can be changed in any desired direction, no bending stress is applied to the expansible links 13, but only compressive load and/or tensile load are applied to the same. This makes it possible to use expansible links 13 having relatively low strength and rigidity, thereby reducing the weight of the parallel linkage 10. Further, the fixed link 11 has the lower end thereof connected to the foot portion 3 via the ball joint 12 such that the angle thereof with respect to the foot portion 3 can be changed in any desired direction, which ensures a high degree of freedom in the angle of relative motion between the living under-knee leg portion and the foot portion 3, to thereby enable e.g. twisting motion of the ankle joint.

Further, according to the parallel linkage 10, each of the coil springs 13c urges the corresponding expansible link 13 in a direction opposite to the expanding direction or the contracting direction of the spring 13c, which makes it possible to reduce shock transmitted to the living body via the expansible links 13. Furthermore, as described hereinabove, when the user tilts the under-knee leg portion forward while walking, the urging forces of the coil springs 13c promote the motion of kicking against the floor by the foot portion 3, and when the user tilts the under-knee leg portion backward, the urging forces of the coil springs 13c promote the motion of moving the knee forward, so that walking motion can be performed more nimbly and smoothly. Moreover, even when the walking motion demands the angle of the ankle to follow up a road surface and a proper holding force of the ankle joint, e.g. in the case of walking up or down a slope, the demanded follow-up performance and holding force can be ensured by the urging forces of the coil springs 13c.

Therefore, the artificial joint device 2 using the parallel linkage 10 constructed as above makes it possible to enhance the degree of freedom in the angle of motion of the ankle joint to a level similar to that of an ankle joint of a living leg, which has been unattainable by the artificial joint device of the conventional artificial leg, to thereby enable the artificial leg 1 to smoothly perform turning motion and the like. Moreover, differently from an artificial joint device of a serial linkage type conventionally used e.g. in a robot, the artificial joint device 2 can realized by using the parallel linkage 10 which is simpler, less expensive, and smaller in size than the serial linkage, without using power supply or electric motor.

Although in the parallel linkage 10 of the above first embodiment, the lower end of the fixed link 11 and the upper and lower ends of each of the expansible links 13 are all connected to the foot portion 3 or the mounting plate 4a via the respective ball joints 12, 14a, 14b, this is not limitative, but joints for use in connecting the links 11, 13 to the foot portion 3 or the mounting plate 4a may be each implemented by any suitable joint which allows the link 11 or 13 to be connected to the foot portion 3 or the mounting plate 4a such that the angle thereof with respect to the foot portion 3 or the mounting plate 4a can be changed in any desired direction. In short, any suitable joint having at least three degrees of freedom may be employed. For instance, joints, such as universal joints, which can perform spherical motion may be used. Further, although in the first embodiment, the coil spring 13c is used as urging means for urging each of the expansible links 13 in opposite directions to respective expanding and contracting directions of the expansible link 13, when the expansible link 13 expands and contracts, this is not limitative, but any urging means may be used which is capable of urging the expansible link 13 in an opposite direction to at least one of the expanding and contracting directions of the expansible link 13. For instance, fluid springs, such as air springs, may be used as the urging means. Further, the number of the expansible links 13 is not limited to four, but any plural number of the expansible links 13 may be used.

Figure 8:
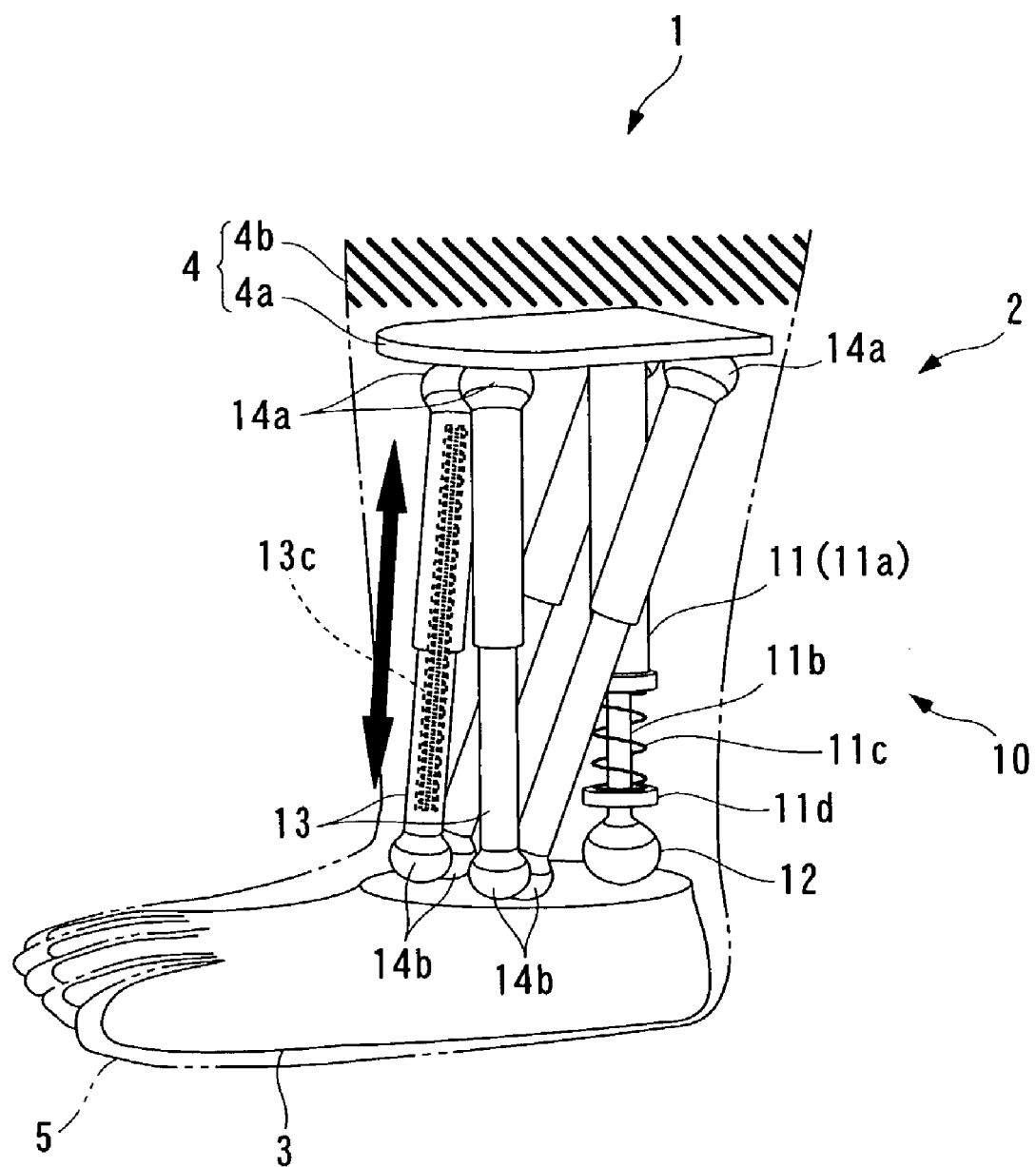
FIG. 8 is a view schematically showing the construction of an artificial leg incorporating an artificial joint device according to a second embodiment of the invention.
Figure 9A:
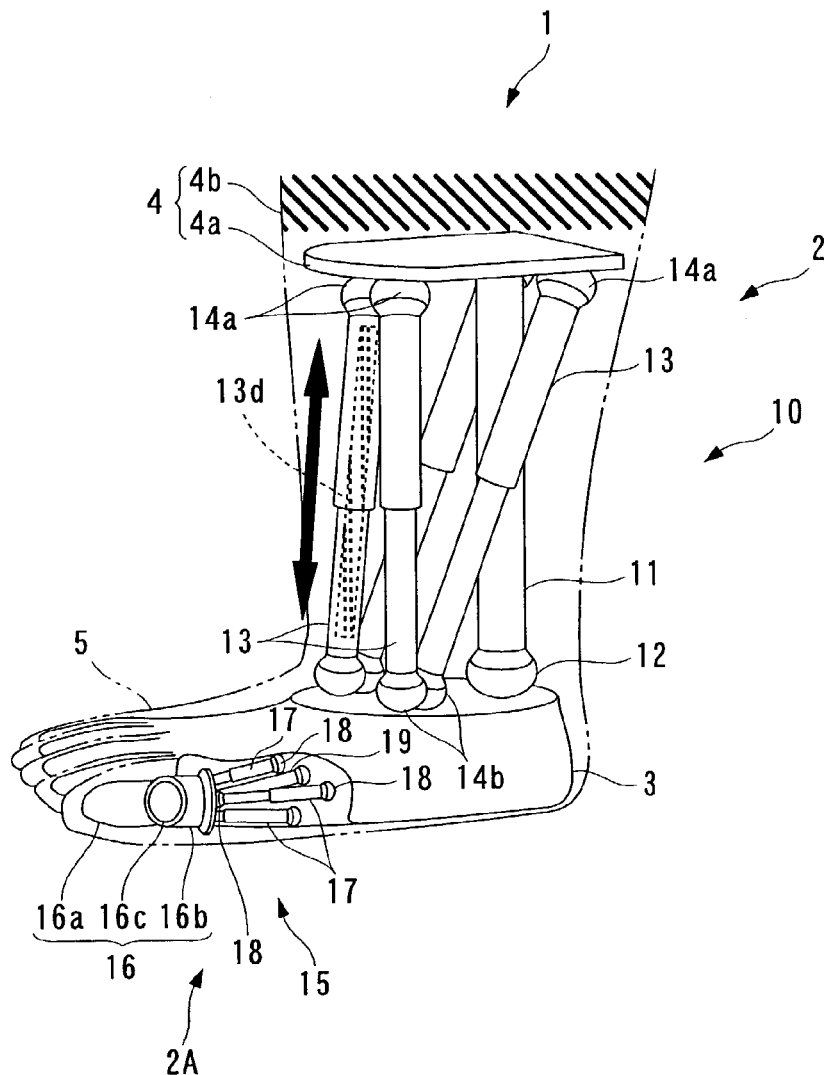
FIG. 9A is a view schematically showing the construction of an automatically controlled artificial leg incorporating an artificial joint device according to a third embodiment of the invention.
Figure 9B:
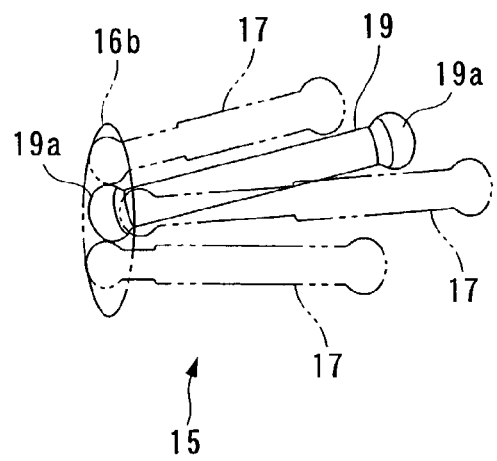
FIG. 9B is a view schematically showing the construction of a parallel linkage for a joint at the ball of the foot.

Next, an artificial joint device 2 according to a second embodiment of the present invention will be described with reference to FIG. 8. It should be noted that in the following description, component parts and elements similar or equivalent to those of the first embodiment are designated by identical reference numerals, and detailed description thereof is omitted when deemed appropriate. As shown in the figure, the artificial joint device 2 of the present embodiment is distinguished from the artificial joint device 2 of the first embodiment only by having a different fixed link 11.

More specifically, the fixed link 11 is expansible, and includes a cylinder 11a, a rod 11b and a coil spring 11c (shock-absorbing member). The cylinder 11a has an upper end fixed to a mounting plate 4a and an open lower end. The rod 11b is fitted in a bore of the cylinder 11a such that the rod 11b can reciprocate within the bore, and has a lower end thereof connected to a foot portion 3 via a ball joint 12.

Further, the rod 11b has a flange 11d formed on a portion upward of a connecting portion thereof via which the rod 11b is connected to the ball joint 12. The coil spring 11c is interposed between the flange 11d and the cylinder 11a in a state wound around the rod 11b, for urging the rod 11b and the cylinder 11a in a direction for expanding a space between the flange 11d and the cylinder 11a.

According to the artificial joint device 2 constructed as above, it is possible to use the urging force of the coil spring 11c to reduce a shock transmitted to the living body of a user wearing an artificial leg 1 via the fixed link 11 by a reaction force from the floor when the user puts the artificial leg 1 onto the floor while walking. Further, this construction makes it possible to reduce a burden on the user wearing the artificial leg 1 including the artificial joint device 2, thereby further improving the user's feeling of wearing or using the artificial leg 1.

Although in the above second embodiment, the coil spring 11c is used as the shock-absorbing member for reducing the shock transmitted to the living body via the fixed link 11, this is not limitative, but the shock-absorbing member may be implemented by any suitable means having a shock-absorbing property. For instance, a fluid spring, such as an air spring, or a synthetic rubber may be employed.

Next, an artificial joint device according to a third embodiment of the present invention will be described with reference to FIGS. 9A to 11B. The artificial joint device of the present embodiment is applied to an artificial joint device for an ankle joint of an electrically controlled artificial leg and an artificial joint device for a joint at the ball of the foot. First, a description is given of the artificial joint device 2 for the ankle joint. This artificial joint device 2 is distinguished from the artificial joint device 2 of the first embodiment in that it includes electrically-driven expansible links 13 and a control system 20 for controlling the expansible links 13.

Figure 10:
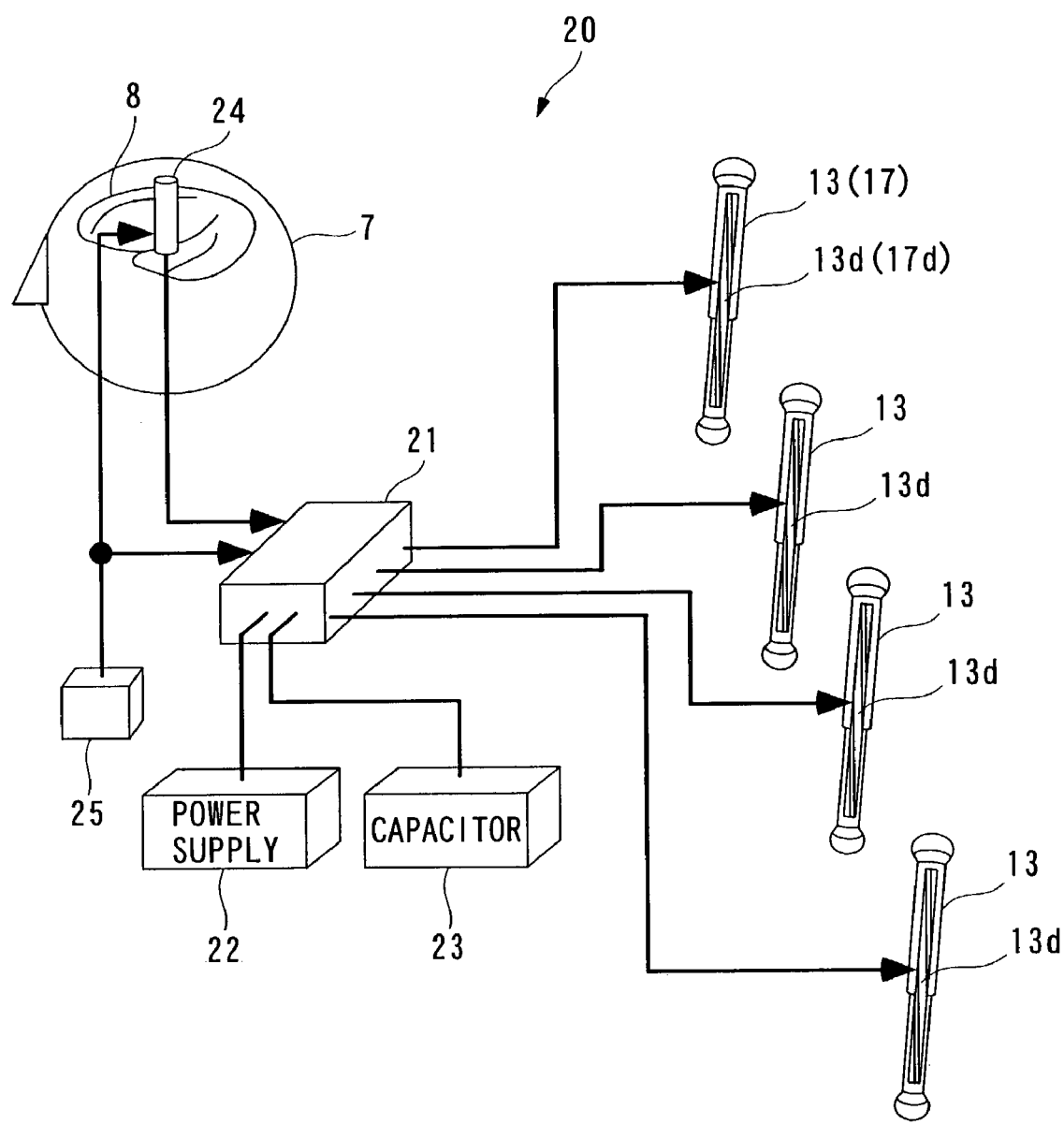
FIG. 10 is a view schematically showing the whole arrangement of a control system for controlling artificial legs.
Figure 11A:
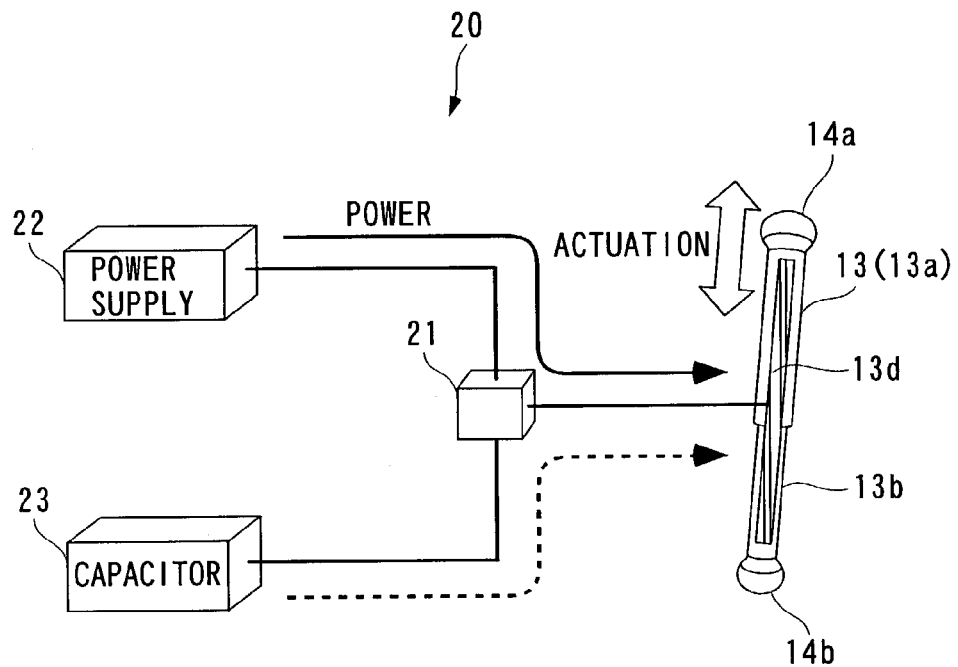
FIGS. 11A and 11B are views useful in explaining operation of an electrically-driven artificial muscle.
Figure 11B:
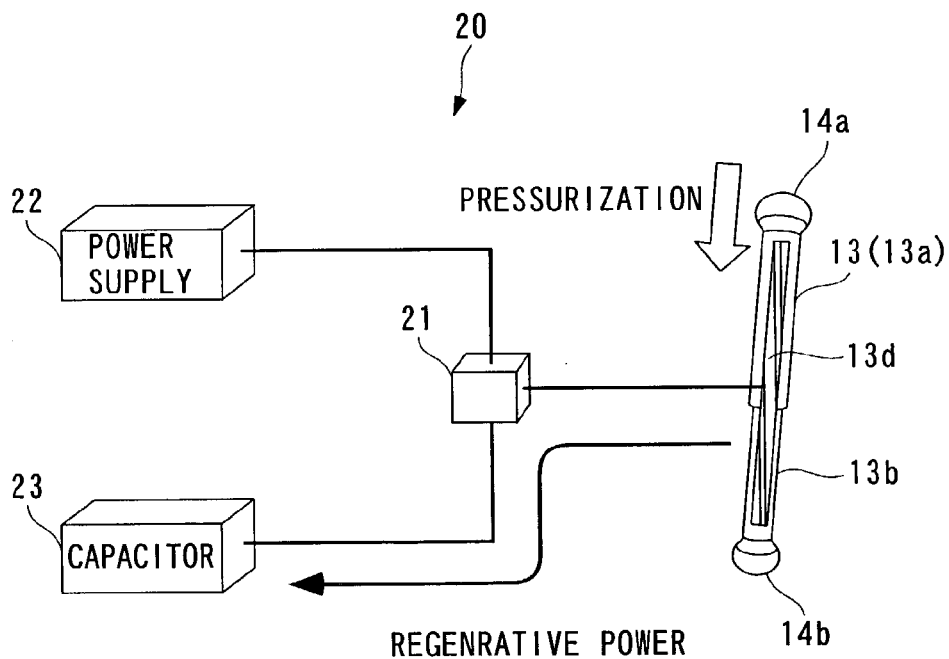

More specifically, as shown in FIGS. 10 and 11A, 11B, each of the expansible links 13 includes an electrically-driven artificial muscle 13d received in two cylinders 13a, 13b. The electrically-driven artificial muscle 13d (actuator) is formed by a polymer actuator composed e.g. of polyacrylonitrile. The electrically-driven artificial muscle 13d expands and contracts in response to input signals to thereby expand and contract the expansible link 13. Further, the electrically-driven artificial muscle 13d is a power regenerative type which produces regenerative electric power by being pressurized.

The control system 20 includes a controller 21 (control means), a power supply 22 (drive source), and a capacitor 23 (accumulator). The electrically-driven artificial muscle 13d is connected to the power supply 22 and the capacitor 23, via the controller 21. The power supply 22 is formed e.g. by a fuel cell. Further, an implant chip 24 (operating will-detecting means) and a joint position sensor 25 are connected to the controller 21.

The implant chip 24 is implanted in a brain 8 of a user 7 of an artificial leg 1. The implant chip 24 detects an instruction from the brain 8, or more specifically an instruction representative of an operating will of the user 7 to operate the artificial leg 1, and delivers a signal indicative of the sensed driver's operating will to the controller 21. Further, the joint position sensor 25 detects an angle position of each of the electrically-driven artificial muscles 13d and delivers a signal indicative of the sensed angle position to the controller 21.

The controller 21 is formed by a microcomputer, and controls electric power supplied to the electrically-driven artificial muscles 13d from the power supply 22 or the capacitor 23, in response to the detection signals from the implant chip 24 and the joint position sensor 25 (see FIG. 11A). Further, when the electrically-driven artificial muscles 13d are producing regenerative power by being pressurized, the controller 21 charges the capacitor 23 with the produced regenerative power and at the same time controls the amount of the regenerative power (see FIG. 11B).

Next, a description will be given of the artificial joint device 2A for the joint at the ball of the foot. The artificial joint device 2A includes a foot portion 3, a hallux (big toe) portion 16 and a parallel linkage 15. The parallel linkage 15 is comprised of three expansible links 17 and a movable link 19.

The hallux portion 16 is comprised of two hallux members 16a, 16b (limb members) and a rotary joint 16c for connecting the two hallux members 16a, 16b such that they are pivotable with respect to each other.

The expansible links 17 are each constructed similarly to the electrically-driven expansible link 13 described above, except that the former is smaller in size than the latter. More specifically, as shown in FIG. 10, each of the expansible links 17 incorporates an electrically-driven artificial muscle 17d (actuator) connected to the controller 21, and has its expanding/contracting operation controlled by the controller 21. Further, each of the expansible links 17 has opposite ends thereof connected to the foot portion 3 and the hallux member 16b of the hallux portion 16, respectively, via respective ball joints 18, 18 (joints for the expansible link).

The movable link 19 is inexpansible, and has opposite ends thereof connected to the foot portion 3 and the hallux member 16b of the hallux portion 16, respectively, via respective ball joints 19a, 19a (joints for the movable link).

Thus, the distance between connecting portions of the foot portion 3 and the hallux member 16b via which the foot portion 3 and the hallux member 16b are connected to the movable link 19, respectively, is held constant even when the expansible links 17 expand or contract.

According to the artificial joint device 2 for an ankle joint, constructed as above, the electrically-driven artificial muscle 13d incorporated in each of the expansible links 13 can be controlled by the controller 21 in response to the detection signals from the implant chip 24 and the joint position sensor 25, which makes it possible to cause the motion of the electrically controlled parallel linkage 10, which is difficult to control directly by an instruction or the like from the brain of the user 7, to match (or conform with) a motion intended by the user 7. In the thus-controlled motion, the angle of motion of the artificial joint device 2 of the artificial leg 1 can be changed by the parallel linkage 10 with a high degree of freedom. In particular, since the respective upper ball joints 14a of the expansible links 13 are arranged such that the ball joints 14a are not positioned in a line on the mounting plate 4a and that the connecting portion of the fixed link 11 via which the fixed link 11 connected to the mounting plate 4a is positioned within a quadrilateral defined by the upper ball joints 14a as vertexes, it is possible not only to twist the artificial joint device 2 as illustrated in FIGS. 7A, 7B, but also to make the expansible links 13 and hence the artificial joint device 2, compact in size.

Similarly to the artificial joint device 2 for an ankle joint, the artificial joint device 2A for the joint at the ball of the foot is capable of controlling the electrically-driven artificial muscle 17d incorporated in each of the expansible links 17 by the controller 21 in response to the detection signals from the implant 24 and the joint position sensor 25, so that it is possible to cause the motion of the electrically controlled parallel linkage 15, which is difficult to control directly by an instruction or the like from the brain of the user 7, to match (or conform with) a motion intended by the user 7. In the motion, the parallel linkage 15 makes it possible to achieve a high degree of freedom in changing the angle of motion of the joint at the ball of the foot of the artificial leg 1, whereby the motion of the hallux portion 16, which plays an important role in turning motion of the artificial leg 1 during walking, can be approximated to that of the hallux of a living foot. Further, since the hallux member 16b of the hallux portion 16 is connected to the foot portion 3 via the inexpansible movable link 19, it is possible to bend the joint at the ball of the foot almost without changing the length of the hallux when the parallel linkage 15 is operated, to thereby further approximate the motion of the joint at the ball of the foot to that of the joint at the ball of the living foot. Thus, the walking motion, including the turning motion, by the automatically controlled artificial leg 1 can be approximated to that of a living leg, thereby enabling smooth walking motion.

Further, since most of the load applied to the artificial leg 1 can be supported by the fixed link 11, it is possible to reduce the respective driving forces of the electrically-driven artificial muscles 13d for driving the corresponding expansible links 13, and reduce the weight of the expansible links 13. In addition, it is possible to produce regenerative power by each artificial muscle 13d when the corresponding expansible link 13 is compressed, so that reduction of both power consumption and the size of the power supply can be achieved. This makes it possible to reduce not only running costs but also the size of the device itself.

Although in the above third embodiment, the implant chip 24 is used as detection means for detecting the signal indicative of the user's operating will, this is not limitative, but any suitable means capable of detecting a user's operating will may be employed as the detection means. For instance, it is possible to use a sensor for detecting changes in a potential of the nervous system, a sensor for detecting the movement of muscles, a sensor for detecting a user's voice, etc.

Further, although in the third embodiment, the movable link 19 is used as means for preventing the length of the hallux from being changed during bending motion of the joint at the ball of the foot, the movable link 19 may be omitted, and expansion and contraction of the expansible links 17 may be controlled by the controller 21 to hold the length of the hallux almost constant during bending motion of the joint at the ball of the foot. This makes it possible to further approximate the bending motion of the joint at the ball of the foot of the present embodiment to that of the joint at the ball of the living foot.

Furthermore, although in the third embodiment, the capacitor 23 is used as an accumulator for storing regenerative power produced by the electrically-driven artificial muscles 13d, this is not limitative, but any suitable means, such as a battery, which is capable of storing the produced regenerative power, may be used as the accumulator.

Figure 12A:
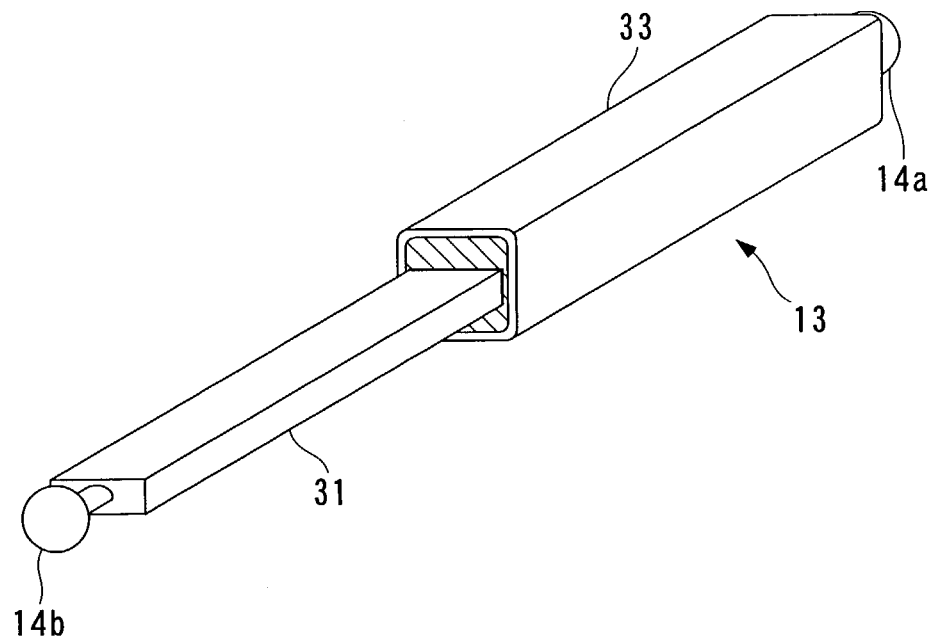
FIG. 12A is a perspective view showing the appearance of an electrically-driven expansible link.
Figure 12B:
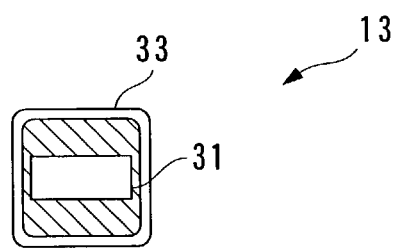
FIG. 12B is a cross-sectional view of the FIG. 12A electrically-driven expansible link.

Moreover, although in the third embodiment, the artificial muscle 13d is used as an actuator for expanding and contracting the corresponding expansible link 13, this is not limitative, but any suitable means capable of expanding and contracting the expansible link 13 may be used as the actuator. For instance, as shown in FIGS. 12A to 12C, a DC linear motor 30 may be used as the actuator for expanding and contracting the expansible link 13.

Figure 12C:
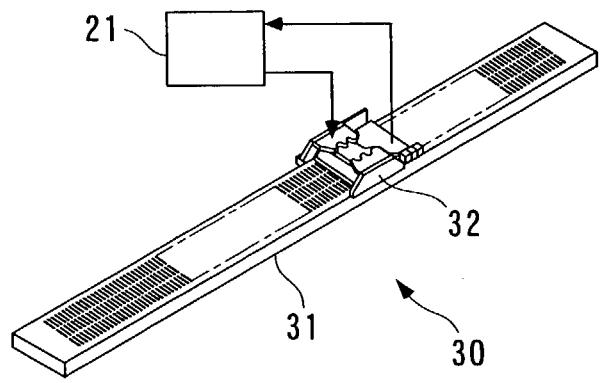
FIG. 12C is a perspective view schematically showing the arrangement of an electric linear motor.

As shown in FIG. 12C, the DC linear motor 30 includes a stator 31 and a mover 32 movable with respect to the stator 31. The mover 32 includes a position sensor, and is connected to the controller 21. Further, as shown in FIGS. 12A, 12B, an expansible link 13 has the stator 31 as an arm and the mover 32 installed therein, and further includes a slider 33 slidable with respect to the stator 31, and ball joints 14a, 14b attached to respective ends of the stator 31 and the slider 33 on opposite sides.

The controller 21 controls the slider 33 in response to a signal from the position sensor of the mover 32 within the slider 33 such that the slider 33 linearly moves with respect to the stator 31, whereby the expansible link 13 is controlled for expansion and contraction. If the expansible links 13 each driven by the DC linear motor 30 described above are used in the parallel linkage 10, it is possible to obtain the same advantageous effects as provided by the parallel linkage 10 of the third embodiment.

Further, when power regeneration by the actuator is not needed, the actuator may be implemented e.g. by an artificial muscle formed of a magnetic shape-memory alloy or a pneumatic-type artificial muscle.

Figure 13:
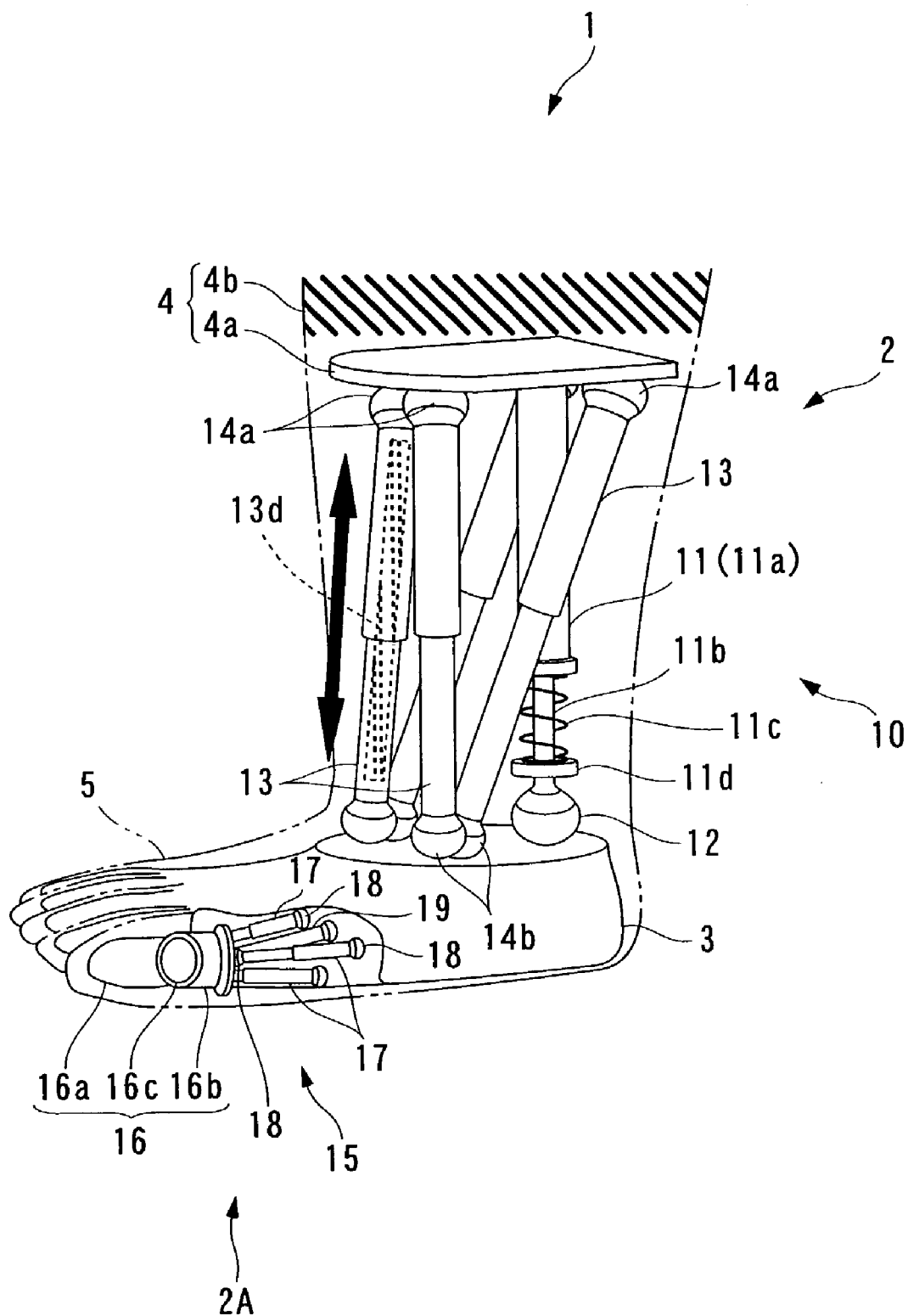
FIG. 13 is a view schematically showing a variation of the artificial joint device according to the third embodiment of the invention.

Further, in the third embodiment, the fixed link 11 may be constructed similarly to the fixed link 11 in the second embodiment as shown in FIG. 13. More specifically, as shown in the figure, the fixed link 11 is expansible, and includes a cylinder 11a, a rod 11b and a coil spring 11c. According to this variation of the parallel linkage 10 according to the third embodiment, the same advantageous effects as provided by the parallel linkage 10 of the second embodiment can be obtained.

Figure 14:
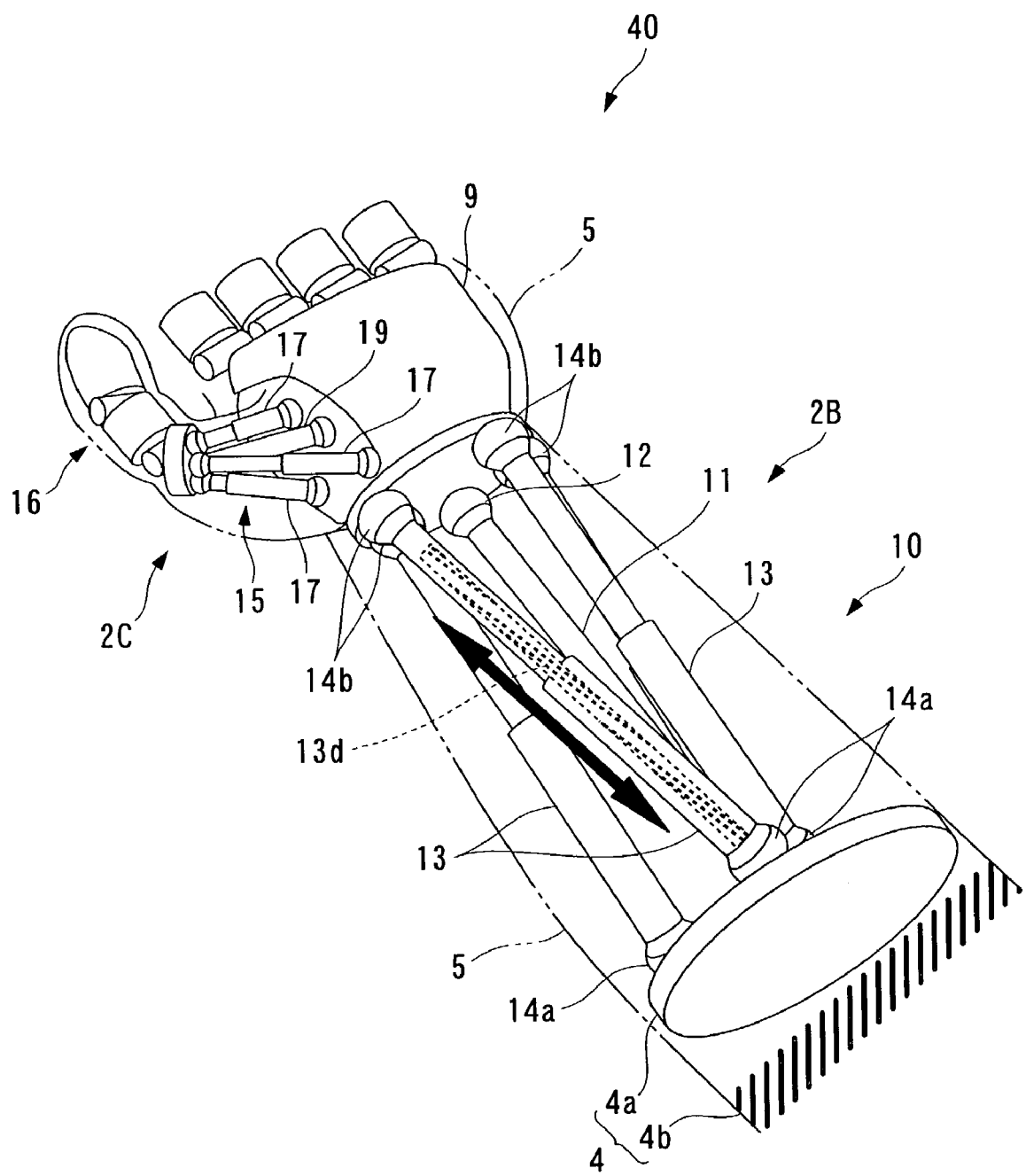
FIG. 14 is a view schematically showing the construction of an automatically controlled artificial arm incorporating an artificial joint device according to a fourth embodiment of the invention.

Next, an artificial joint device according to a fourth embodiment will be described with reference to FIG. 14. As shown in the figure, the artificial joint device of the present embodiment is applied to an artificial joint device for a wrist joint and a joint at a thenar of an artificial arm. The artificial joint device 2B for the wrist joint of the artificial arm 40 is comprised of a hand portion 9 (limb member), a mounting plate 4a, and a parallel linkage 10 connecting the hand portion 9 and the mounting plate 4a. The parallel linkage 10 is an electrically controlled type similar to the parallel linkage 10 of the third embodiment, and has its operation controlled by a control system similar to the control system 20 described hereinabove. In short, the artificial joint device 2B is constructed similarly to the artificial joint device 2 for an ankle joint according to the third embodiment except that the foot portion 3 is replaced by the hand portion 9.

Therefore, the artificial joint device 2B for a wrist joint can provide the same advantageous effects as obtained by the artificial joint device 2 of the third embodiment. More specifically, the artificial joint device 2B makes it possible to cause the motion of the electrically controlled parallel linkage 10, which is difficult to control directly by an instruction or the like from the brain of a user, to match (or conform with) a motion intended by the user. In the motion, it is possible to change the angle of motion of the artificial joint device 2B of the artificial arm 40 by the parallel linkage 10, with a high degree of freedom.

An artificial joint device 2C for the joint at a thenar is comprised of a hand portion 9, a thumb portion 16, and a parallel linkage 15 connecting the hand portion 9 and the thumb portion 16. The artificial joint device 2C is constructed similarly to the artificial joint device 2 for the joint at the ball of the foot according to the third embodiment except that the foot portion 3 is replaced by the hand portion 9 and that the thumb portion 16 is slightly different in construction from the hallux portion 16. Therefore, the artificial joint device 2C for the joint at a thenar can provide the same advantageous effects as obtained by the artificial joint device 2A for the joint at the ball of the foot according to the third embodiment. More specifically, the artificial joint device 2C makes it possible to cause the motion of the electrically controlled parallel linkage 15, which is difficult to control directly by an instruction or the like from the brain of a user, to match (or conform with) a motion intended by the user. In the motion, the parallel linkage 15 makes it possible to achieve a high degree of freedom in changing the angle of motion of the joint at the thenar, and hence the motion of the thumb portion 16, which plays an important role in grasping motion, can be approximated to that of the thumb of a living hand.

Although in the above third and fourth embodiments, the artificial joint device of the invention is applied to the artificial leg and the artificial arm, this is not limitative, but the artificial joint device is applicable to an artificial limb of a robot, a manipulator, and the like.

It is further understood by those skilled in the art that the foregoing are preferred embodiments of the invention, and that various changes and modifications may be made without departing from the spirit and scope thereof.

What is claimed is:

1. In combination, a parallel linkage for connecting two link mounting portions spaced from each other, comprising:
    a fixed link having one end thereof fixed to one of the link mounting portions;
    a fixed-link joint for connecting another end of said fixed link to another of the link mounting portions such that an angle of said fixed link with respect to the another of the link mounting portions can be changed in any desired direction;
    a plurality of expansible links extending between the two link mounting portions in an expansible/contractible manner, wherein said plurality of expansible links are at least three expansible links;
    a plurality of expansible-link joints respectively connecting opposite ends of said plurality of expansible links to the link mounting portions such that respective angles of each expansible link with respect to the link mounting portions can be changed in any desired direction
    a drive source;
    actuators each for actuating a corresponding one of said at least three expansible links for expansion and contraction by a driving force supplied from said drive source, wherein said each actuator is an electric actuator configured to produce regenerative power when said corresponding expansible link is expanded and contracted by an external force;
    control means for controlling said driving force supplied to said each actuator from said drive source; and
    an accumulator for storing the regenerative power produced by each said electric actuator.

2. A parallel linkage according to claim 1, further comprising urging members provided in said plurality of expansible links, respectively, each for urging a corresponding one of said expansible links in at least one opposite direction to directions in which said expansible link expands and contracts, when said expansible link expands and contracts.

3. A parallel linkage according to claim 1, wherein said at least three expansible links are arranged such that connecting portions thereof connected to at least one of the two link mounting portions are not in a line on the at least one of the two link mounting portions, and that a connecting portion of said fixed link is positioned within a polygon defined by the connecting portions of said at least three expansible links as vertexes.

* * * * *